US00PP12236P2

(12) United States Plant Patent
Drewlow

(10) Patent No.: US PP12,236 P2
(45) Date of Patent: Nov. 27, 2001

(54) NEW GUINEA IMPATIENS PLANT NAMED 'OVATION RED PEPPERMINT'

(75) Inventor: Lyndon W. Drewlow, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/550,518

(22) Filed: Apr. 17, 2000

(51) Int. Cl.[7] ..... A01H 5/00

(52) U.S. Cl. ..... Plt./318

(58) Field of Search ..... Plt./318

*Primary Examiner*—Bruce R. Campell
*Assistant Examiner*—Anne Marie Grünberg
(74) *Attorney, Agent, or Firm*—Webb Ziesenheim Logsdon Orkin & Hanson, P.C.

(57) ABSTRACT

A distinct cultivar of Impatiens plant named Ovation Red Peppermint, characterized by its red and lavender bicolored flower color, oval-shaped leaves, continuous, and long-lasting flowering, self-branching and vigorous habit.

1 Drawing Sheet

The present invention relates to a new and distinctive cultivar of Impatiens plant. botanically known as *Impatiens hawkeri*, commercially known as New Guinea Impatiens, and known by the cultivar name 'Ovation Red Peppermint'. Ovation Red Peppermint was developed in a controlled breeding program by crossing Mikkelsen Seedling No. 95-264-3 (seed parent) with Mikkelsen Seedling No. 94-604-1 (pollen parent). The seed and pollen parents are proprietary breeding lines which have not been sold or made publicly available in this country.

Asexaul reproduction carried out by the inventor in Lompoc, Calif. by terminal or stem has shown that the unique features of this new Impatiens are stabilized and are reproduced true to type in successive propagations.

The following combination of characteristics distinguishes the new Impatiens from both its parent varieties and other cultivated Impatiens of this type known and used in the floriculture industry:

1. Ovation Red Peppermint has red (Red Group 46B) and lavender (Purple-Violet Group 80C) bicolored flowers while Neptis (U.S. Plant Pat. No. 10,321) has lighter bicolored flowers of Red Group 42A and Red-Purple Group 62C.

2. Ovation Red Peppermint has a spur that is entirely yellow-green in color while Neptis has a spur with a reddish cast on the upper third of the spur.

3. Ovation Red Peppermint has an oval leaf while Neptis has a lanceolate leaf.

4. Ovation Red Peppermint has a small leaf length (7 to 8 cm) in comparison to the length of the Neptis leaf (10 to 11 cm), and they have similar widths (4.0 to 4.5 cm).

5. Ovation Red Peppermint has a heavy brown-purple cast to the upper and lower leaf surfaces while Neptis has only a slight reddish cast.

6. Ovation Red Peppermint has a more mounded growth habit and is more compact than Neptis, which is taller and more upright.

7. The hood of the anther of Ovation Red Peppermint has more red pigmentation than Neptis.

8. Ovation Red Peppermint has shorter flower pedicles (3.5 cm) while Neptis has longer pedicels (4.5 cm).

The accompanying colored photograph illustrates the overall appearance of this cultivar taken as a face view of the plant and showing the colors as true as it is reasonably possible to obtain in a colored reproduction of this type.

The following is a detailed description of my new cultivar, based on plants produced in greenhouses in Lompoc, Calif. during the Fall–Winter season of the year. Plants were grown in 15 cm pots and measurements were taken 20 weeks after rooted cuttings were planted. Height measurements were taken from the soil line of the container. The plants were grown at 61° C. night temperatures, under 3000 to 4000 foot candles of light and with nutritional trace elements added. Habit of growth, foliage coloration, leaf variegation, size of leaves and flower size will be greatly influenced by nutritional and environmental conditions.

Color references are made to The Royal Horticultural Society Colour Chart except where general terms of ordinary significance are used.

Parentage: A controlled cross between female parent Mikkelsen Seedling No. 95-264-3 and male parent Mikkelsen Seedling No. 94-604-1.

Propagation:

(*A*) *Type cutting.*—Stem tip 15 mm long will develop to 4 to 5 cm long in 18 to 21 days.

(*B*) *Time to root.*—8–10 days at 23° C. summer; 10–12 days at 20° C. winter.

(*C*) *Rooting habit.*—Heavy, fibrous.

Plant description:

(*A*) *Form and habit of growth.*—Mounded to semi-upright, self-branching, intermediate in height, flowers open over the top of leaf canopy; continuous flowering; vigorous growing flowering herb. Average height is 18 to 22 cm and average width is 45 to 50 cm. Internode length is 4.5 to 5.5 cm but is highly variable. Pedicel is Greyed-Purple Group 184C, stem is Yellow-Green Group 146A, and internode is Yellow-Green Group 146A. Pedicel length is 3.5 cm.

(*B*) *Foliage description.*—Dark green leaves with brownish-red cast; red-purple midrib and no leaf variegation. (1) Size: 7 to 8 cm long and 4 to 4.5 cm wide on average mature leaf. (2) Shape: Oval with acuminate apex and acute base. (3) Texture: Both upper and lower surface are glabrous. (4) Margin: Entire, with fine [ciliate] cilia. (5) Color: Young foliage, top side is Yellow-Green Group 147A, underside is Greyed-Purple Group 183A. Mature foliage, top side is Yellow-Green Group 147A, underside is Greyed-Green Group 183A. (6) Venation: Pinnate, upper side is Greyed-Purple Group 184C and lower side is Greyed-Purple Group 185A. (7) Young midrib is Greyed-Purple Group 184C and mature midrub is Greyed-Purple Group 184D.

(*C*) *Branching.*—The branching is naturally occurring. Lateral branching at base: 5 or more lateral branches. Lateral branch length is 15 to 18 cm but is highly variable.

Flowering description:

(*A*) *Flowering habits.*—Flowers continuously from leaf whorl in a progressively orderly manner with one flower per leaf axil. When the last flower in a whorl opens, the first flower in the leaf whorl above starts to open. It takes 5 to 7 days for a mature bud to fully open and the flower may last two weeks or longer depending on the environment. The time to first flower is approximately 8 weeks from root cuttings. The flowers are self-cleaning.

(*B*) *Natural flowering season.*—Indeterminate and continuous; quantity of flowering increases with increasing levels of light.

(*C*) *Flower bud.*—Ellipsoidal; flowers perfect; spur is 5.0 cm long on mature bud, with the throat behind the ovary and originating from the major sepal. Bud length is 18 to 20 mm and bud diameter is 15 mm. Spur is Yellow-Green Group 147C, spur tip is Yellow-Green Group 146B, flower bud is Red Group 46A just before opening, and eye is Red Group 46B.

(*D*) *Flowers borne.*—On individual yellow-green pedicles 3.5 cm long from a whorl of usually five leaves. Flowering progressively around the whorls as buds and leaves develop. Leaf axils have one flower each.

(*E*) *Quantity of flowers.*—Numerous because of self-branching nature of plant and the long-lasting flower characteristic.

(*F*) *Diameter of flower.*—6.0 to 6.5 cm. Flower Depth: 5 mm.

(*G*) *Petals.*—Shape: Heart; standard petal is largest. (2) Color: Top side when opening is bicolored of Red Group 46B around midrib and Purple-Violet Group 80C at edges of petal; fading to Red Group 46B around midrib and Purple-Violet Group 80D; underside is Red Group 51A. (3) Number of petals: Five. (4) Size of petals: Standard: 4.5 cm wide and 2.5 cm long, two equal lobes with shallow cut. Wings: 3.0 cm wide and 3.0 cm long, two unequal lobes with moderate cut. Keel: 4.0 cm wide and 3.0 cm long, two unequal lobes with moderate cut.

(*H*) *Reproductive organs.*—(1) Stamens: Five in number. (a) Anther: Hooded shape, color is Yellow-White Group 158A with a Red-Purple Group 66C cast. (b) Pollen color: Yellow-White Group 158C. (2) Pistils: (a) Stigma: Five, segmented column, color is Red-Purple Group 64C. (b) Style color: Reddish-purple. (c) Ovaries: Five in number, size is 5 mm when immature, color is Greyed-Purple Group 185A.

(*I*) *Fertility.*—The plants are fertile, but do not normally set seed under greenhouse or garden conditions, unless in a controlled crossing program.

Disease resistance: No significant disease or insect problems seen to date.

I claim:

1. A new and distinct variety of Impatiens plant named Ovation Red Peppermint, as illustrated and described.

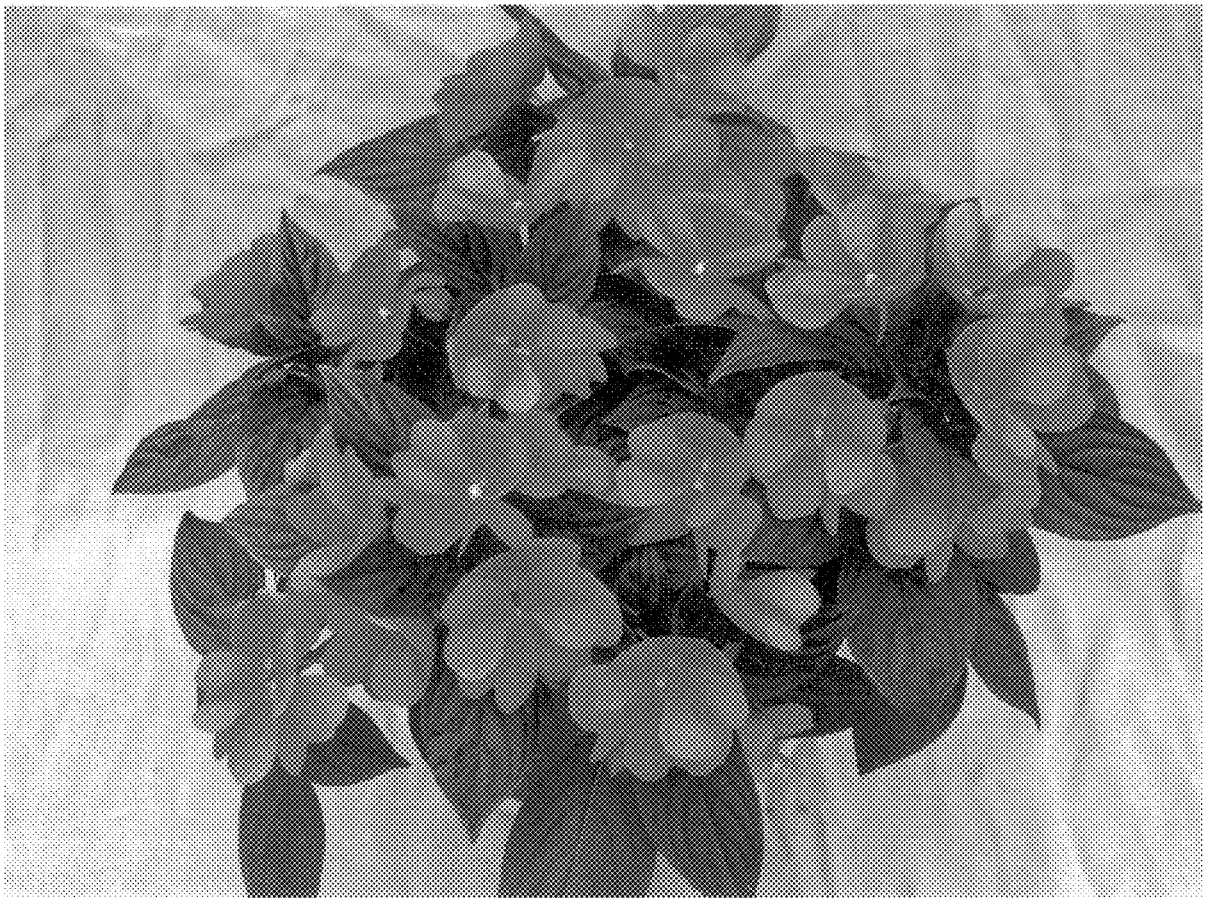

* * * * *